United States Patent [19]
Rantala

[11] Patent Number: 5,479,923
[45] Date of Patent: Jan. 2, 1996

[54] METHOD AND APPARATUS FOR ANALYZING A SAMPLE

[75] Inventor: Börje T. Rantala, Helsinki, Finland

[73] Assignee: Instrumentarium Corporation, Finland

[21] Appl. No.: 137,670

[22] Filed: Oct. 15, 1993

[30] Foreign Application Priority Data

Oct. 16, 1992 [FI] Finland .................... 924716

[51] Int. Cl.⁶ ........................................ A61B 5/00
[52] U.S. Cl. ........................................ 128/632; 128/637
[58] Field of Search .................... 128/633–635, 128/637, 664–665, 632; 436/50

[56] References Cited

U.S. PATENT DOCUMENTS

| | | | |
|---|---|---|---|
| 4,221,567 | 9/1980 | Clark et al. | 23/230 |
| 4,233,513 | 11/1980 | Elder et al. | 250/343 |
| 4,273,636 | 6/1981 | Shimada et al. | 204/195 |
| 4,423,739 | 1/1984 | Passaro et al. | 128/719 |
| 4,424,276 | 1/1984 | Clark et al. | 436/50 |
| 4,480,190 | 10/1984 | Burough et al. | 250/343 |
| 4,576,590 | 3/1986 | Fiddian-Green | 604/26 |
| 4,596,931 | 6/1986 | Ehnholm et al. | 250/343 |
| 4,643,192 | 2/1987 | Fiddian-Green | 128/632 |
| 4,671,287 | 6/1987 | Fiddian-Green | 128/631 |
| 4,677,143 | 6/1987 | Laurin et al. | 523/122 |
| 4,859,858 | 8/1989 | Knodle et al. | 250/504 |
| 4,859,859 | 8/1989 | Knodle et al. | 250/343 |
| 4,907,166 | 3/1990 | Corenman et al. | 364/497 |
| 4,914,720 | 4/1990 | Knodle et al. | 250/343 |
| 5,042,522 | 8/1991 | Corenman et al. | 137/239 |
| 5,067,492 | 11/1991 | Yelderman et al. | 128/719 |
| 5,095,913 | 3/1992 | Yelderman et al. | 128/719 |
| 5,158,083 | 10/1992 | Sacristan et al. | 128/635 |
| 5,174,290 | 12/1992 | Fiddian-Green | 128/632 |
| 5,186,172 | 2/1993 | Fiddian-Green | 128/632 |

FOREIGN PATENT DOCUMENTS

| | | |
|---|---|---|
| 340908 | 11/1989 | European Pat. Off. . |
| 2534255 | 3/1976 | Germany . |
| 9001894 | 3/1980 | WIPO . |
| 9001893 | 3/1990 | WIPO . |
| 9210971 | 7/1992 | WIPO . |

OTHER PUBLICATIONS

Boda, D. and Muranti, L. "Gastrotonometry, An Aid To The Control Of Ventilation During Artificial Respiration" published in *The Lancer*, 1959, London, Great Britain, pp. 181–182.

NORMOCAP 200 specification by Instrumentarium Corporation, published Jun., 1989.

Primary Examiner—Angela D. Sykes
Attorney, Agent, or Firm—Andrus, Sceales, Starke & Sawall

[57] ABSTRACT

The invention relates to an apparatus and a method for analyzing a compound to be drawn from a patient's organ. The apparatus comprises a sampling element having a wall which a compound to be analyzed is capable of penetrating. The apparatus also includes a pressure-difference producing element which, through the action of a pressure-difference, is capable of delivering a sample along a tube extending from the sampling element. The apparatus also includes an analyzer capable of performing an analysis on a sample drawn from the sampling element. The analyzer is in flow communication with the sampling element by way of the tube. According to the method, a mixture consisting of a medium and a compound drawn from the organ is delivered to the analyzer for a subsequent analysis, and at least some of the mixture is returned from the analyzer back to the sampling element.

37 Claims, 2 Drawing Sheets

METHOD AND APPARATUS FOR ANALYZING A SAMPLE

BACKGROUND OF THE INVENTION

The present invention relates to an apparatus and a method for analyzing a compound sampled from the organ of a patient. The apparatus includes a sampling element, having a wall which is permeable to a compound to be analyzed which is thus capable of transferring from the organ into a sample chamber included in the sampling element, a means for producing a pressure difference and capable of using the pressure difference for aspirating sample from the sample chamber along a tube extending from the sampling element, and an analyzer capable of carrying out the analysis of a sample delivered from the sampling element.

In current technology, oxidation of the peritoneum is monitored by measuring the intra-abdominal carbon dioxide level and hemal bicarbonate by using discrete blood and buffer liquid samples.

The concentration of a patient's inner organ gas, especially CO2, is measured by drawing samples from the vicinity of this inner organ, e.g. from the abdomen, said samples being analyzed in a laboratory analyzer. According to the solution described in U.S. Pat. No. 4,643,192, the sampling is effected by means of a catheter. The catheter consist of a sampling element, having a wall through which the gas is absorbed into a salt solution contained inside the catheter and which wall is not permeable to a liquid component, and of a tube for aspirating a sample from the sample chamber and for delivering a fresh salt solution into the sample chamber. The aspiration and supply of a liquid into the tube and sample chamber is effected by means of a syringe connected to a special fitting mounted on the end of the tube. The liquid contained in the sampling element must be allowed a relatively long time, e.g. half an hour, for the interaction with an outside gas to be measured in order to provide a sufficient time for the gas to absorb through the sampling element wall and to reach an equilibrium. This is followed by aspirating the liquid out of the catheter into the syringe and by taking it to a laboratory for analysis for the determination of the concentration of a gas diffused through the catheter wall.

A problem in this type of solution is the execution of the measurement of a gas penetrated through the catheter wall, the method being inconvenient and tedious. This tediousness and inconvenience is further emphasized by the fact that every time the catheter is exhausted of liquid by suction said catheter must be refilled with fresh liquid, which must be allowed to stay in the catheter for a sufficiently long time in order to reach a gas equilibrium before it is aspirated out and transferred for analysis.

SUMMARY OF THE INVENTION

An object of this invention is to eliminate the above problems. The object is to provide a high-speed method and apparatus for analyzing a compound found in the organ of a patient. Another object is to provide a simple method and apparatus for analyzing a compound found in the organ of a patient. A further object is to provide such a method and apparatus for analyzing a compound found in the organ of a patient that the delivery of a sample from a sampling location to a measurement-effecting element proceeds automatically. A still further object is to provide such a method and apparatus for analyzing a compound found in the organ of a patient that the passage of a sample can proceed back and forth between a sampling location and a measurement effecting element. A particular object is to provide such a method and apparatus for analyzing a compound found in the organ of a patient which facilitates an automatically proceeding, continuous measuring action. A quite special object is to provide a method and apparatus for measuring the concentration of a compound found in the organ of a patient.

The characterizing features of a method and apparatus of the invention are set forth in the appended claims.

According to the invention, a sampling element is placed in the organ of a patient, e.g. in the stomach, and a sample is drawn from this environment into this sampling element for further delivering the sample along a tube to an analyzer for the analysis of one or more compounds found in the sample. The analysis may include the determination of a compound concentration and/or the identification of a compound. A particular object is to analyze the carbon dioxide content. The sampling element can be inserted into the stomach of a patient without any major surgical procedures directly through the mouth of a patient. At least during the insertion phase through the pharynx and esophagus of a patient, the sampling element should have a sufficiently narrow cross-diameter, so that its passage to and from a sampling location would be as pleasant as possible for a patient.

A sample arriving in the sampling element should preferably be capable of being restricted to either a liquid or gaseous state for leaving the material in the other physical state outside the sampling element. Thus, in an effort to analyze the carbon dioxide content, only a sample representing the gaseous state should be capable of penetrating into the sampling element. Therefore, the sampling element can be surrounded with a wall, permeable to gas but preferably as impermeable as possible to liquid and consisting e.g. of silicone.

The sampling can be effected either by aspiration or most preferably by allowing a compound outside the sampling element to gradually diffuse into the sampling element eg. through a wall surrounding the same. In an effort to carry out the determination of content or concentration, the diffusion is usually allowed to continue for as long as it takes to reach a state of equilibrium between the sampling element and its environment, the concentration thus being at least nearly equal both in the sampling element and in the environment. Inside the sampling element there must be some medium, such as e.g. a liquid or a gas, for mixing therewith a compound coming from outside. When measuring the carbon dioxide content, one suitable medium is a gas, for example air.

For analysis, a sample is delivered from the sampling element by means of a pressure difference to an analyzer, which can be e.g. an infrared analyzer. The pressure difference can be produced e.g. by means of a manually or electrically operated pump. Preferably, the sampling element has a direct communication with the analyzer by way of a tube. The sampling element can be refilled either with a fresh medium or preferably with the same mixture of a medium and a compound, or a sample, to be examined. Delivering the same mixture of a medium and a compound to be examined, already subjected to analysis, offers a benefit at least when the question is about monitoring the variations occurring in the content of some compound, such as carbon dioxide. In this case, the previous mixture is likely to have a content which is closer to a current new content reading than that of a fresh medium, which is why the equilibrium is reached more quickly by circulating a mixture of the old medium and a compound to be examined between the sampling element and the analyzer. After all, according to the most preferred embodiment, the passage of a compound to be examined can occur into and out of the sampling element. The delivery of a fresh medium or a mixture of a previously examined sample and a medium into the sampling element can be carried out along a tube which is the same as or different from the one used for aspirating a sample to an analyzer.

In view of measuring a pressure prevailing in the analyzer, a chamber in flow communication with the analyzer is fitted with a pressure-measuring element. The analyzer is in turn located most preferably between a sampling element and a pressure-difference producing element, when the latter element is considered to be included therein. The pressure measuring element measures a pressure prevailing in the analyzer whenever it is possible to obtain a pressure reading corresponding to the sampling moment, since the pressure fluctuation has a considerable effect particularly on the content measuring results. In the most preferred case, the measurement of pressure is effected at the moment of analysis. The measured pressure reading can be used for the calculative correction of a content measuring result. The calculative correction of the result can be effected either manually or preferably by means of a processor.

According to a preferred embodiment of the invention, during the analysis of a gas the concentration of water vapor coming from a sampling element and mixed with a medium is allowed to balance itself with ambient air. This can be accomplished by means of a wall, fitted between a sampling element and a pressure-difference producing element and made of a water-permeable material. It permits the passage of water from a location with more water to a location with less water. This wall may form at least a part of a tube extending from the sampling element. The purpose of removing excess water is to avoid the distortion of a measuring result which is due to the condensation of water usually occurring in an analyzer.

BRIEF DESCRIPTION OF THE DRAWINGS

The invention will now be described in more detail with reference made to the accompanying drawings, in which FIG. 1. a schematic view of an embodiment of the invention for analyzing a sample to be drawn from the organ of a patient, FIG. 2. shows one alternative embodiment of the invention for analyzing a sample to be drawn from the organism of a patient, FIG. 3. shows yet another alternative embodiment of the invention for analyzing a sample to be drawn from the organ of a patient.

DETAILED DESCRIPTION OF THE DRAWINGS

Figure 1:
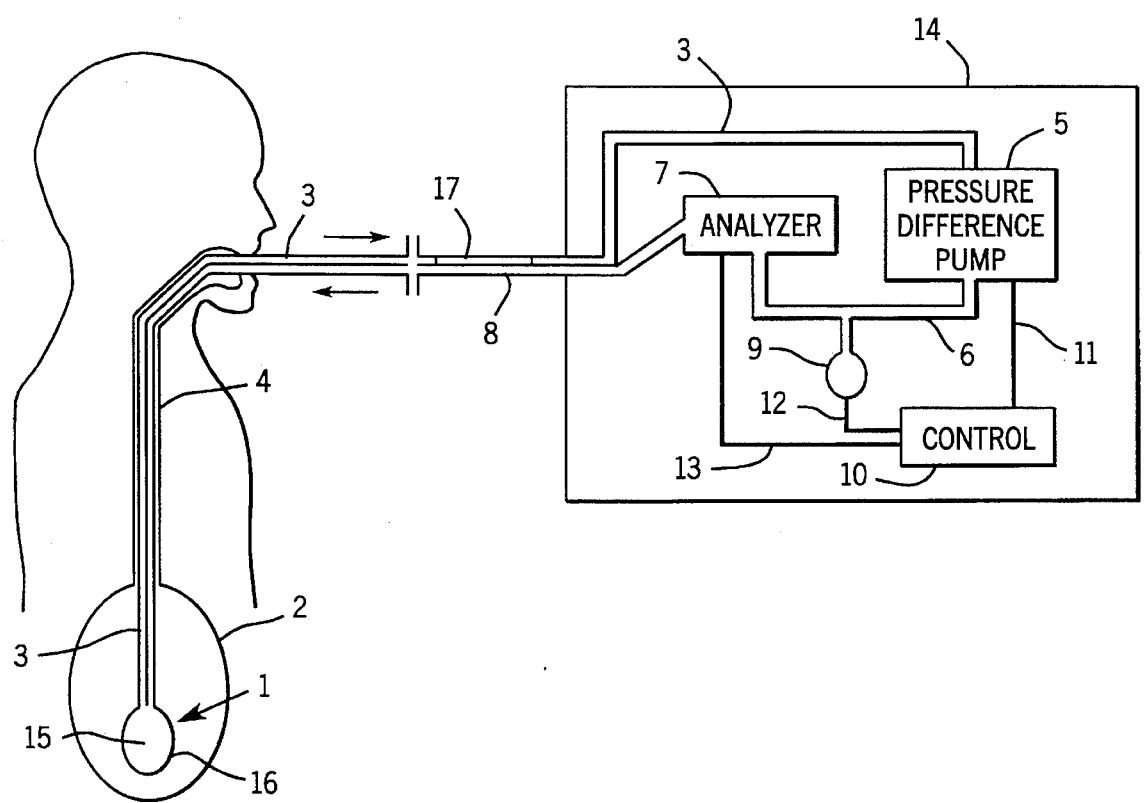

In FIG. 1, a sampling element 1 has been inserted in a patient's organ 2, which in this case is the stomach. From the sampling element extends a tube 3 through a patient's esophagus 4 to a pressure-difference producing element 5, such as e.g. a pump, for aspirating a sample contained in the sampling element. From this element along a tube 6 the sample is delivered to an analyzer 7 for measuring the content of one or more components included in the sample. The analyzer could just as well be used for the identification of a compound. As shown in FIG. 1, a sample coming from the analyzer is preferably delivered along a tube 8 back to sampling element 1. A gas chamber in communication with the analyzer is also provided with a pressure-measuring element 9. In one preferred embodiment of FIG. 1, said element 9 is in communication with analyzer 7 through the intermediary of tube 6. Tube 6 is located between the analyzer and pressure-difference producing element S.

Also illustrated in FIG. 1 is a control unit 10, preferably a microprocessor. The control unit is connected by way of lines 11, 12 and 13 with pressure-difference producing element 5, pressure-measuring element 9 and analyzer 7, respectively. In the preferred embodiment shown in FIG. 1, said pressure-difference producing element 5, pressure-measuring element 9, analyzer 7 and control unit 10 are components included in a special monitor 14. Thus, the analyzer 7 included in this monitor is in direct communication with sampling element 1.

Sampling elements suitable for the purpose of this invention are commercially available, so the construction thereof is not described in detail in this specification. U.S. Pat. No. 4,643,192 discloses one such solution. These products are sold by Tonometrics, Inc., USA.

In order to be functional the solution of FIG. 1 requires a medium for mixing therewith a compound or a sample absorbed from the stomach into sampling element 1. The medium can be a gas, e.g. air, for measuring the carbon dioxide content of the stomach. The sampling element is preferably sealed for blocking a direct flow from outside but allowing, however, the diffusion of a desired compound, in this case carbon dioxide, in a medium contained inside the sampling element in a sample chamber 15. This is why a medium contained inside the sampling element is separated from the space remaining outside the sampling element usually by means of a wall 16, which is permeable to a compound, such as carbon dioxide, which in gaseous state, but is not permeable to liquid at least to a significant degree. Diffusion occurring through the wall leads to the situation that the partial pressures of carbon dioxide on either side of the wall are gradually equalized.

Preferably, as the carbon dioxide content in a sampling element has reached a maximum value prevailing at that particular moment, said pressure-difference producing element 5 is used for delivering a sample from sampling element 1 to analyzer 7 along tube 3 and 6. A message reporting the result of a carbon dioxide measurement proceeds to control unit 10 the same way as a pressure reading message received from pressure-measuring element 9. The control unit processes the received measuring results to calculate a carbon dioxide content corrected with the pressure reading. The result of analysis effected by means of analyzer (7) is corrected to match a predetermined pressure condition when said pressure-measuring element 9 detects that the pressure reading of a mixture contained in the analyzer differs from the predetermined pressure condition. Such correction can be effected according to the following formula:

| | |
|---|---|
| $P_{CO2,real} =$ | $P_{CO2,meas} * P_1/P_0$, wherein |
| $P_{CO2,meas} =$ | analyzer measurement |
| $P_1 =$ | measured pressure (pressure in sampling element) |
| $P_0 =$ | predetermined pressure condition |

A measured sample is delivered from the analyzer back to sampling element 1 along a tube 8 still by means of pressure-difference producing element 5. Thus, in this preferred embodiment, a sample returns to the sampling element along a tube other than the one used for the aspiration of a sample there from to the analyzer. Since the carbon dioxide content of a mixture containing a medium and carbon dioxide is now close to the carbon dioxide content of the organ, it is possible to attain considerably more quickly than at the start of the process a partial carbon dioxide pressure inside the sampling element which corresponds to the current condition of the organism at that particular moment. The control unit can be used for controlling the operation of a pressure-difference producing element e.g. in a manner that the operation of pressure-difference producing element is actuated at certain intervals for periodically drawing a sample from a sampling element, or in a manner that a pump produces a continuous suction, whereby a mixture formed by a sample and a medium circulates all the time from sampling element to analyzer and back again. This way it is possible to monitor continuously the variations occurring in the carbon dioxide level.

FIG. 1 shows one preferred solution for removing the moisture collected in a sample. A medium contained in sampling element 1 may collect water vapor diffused from the organ along with carbon dioxide. The water vapor may condense on the analyzer windows and impair the intended measurement. Therefore, a sample coming from the sampling element can be guided preferably upstream of the analyzer past a wall 17 made of a water-vapor-permeable material, said wall equalizing the partial pressure of water vapor to match the ambient air. Said wall 17 can be a part of tube 3 or the wall may comprise a separate tube, which is attached to tube 3 and through which a sample flows. For example, E. I. du Pont de Nemours and Company, Del., U.S. manufactures a water-vapor permeable material, sold under the trademark Nafion.

Figure 2:
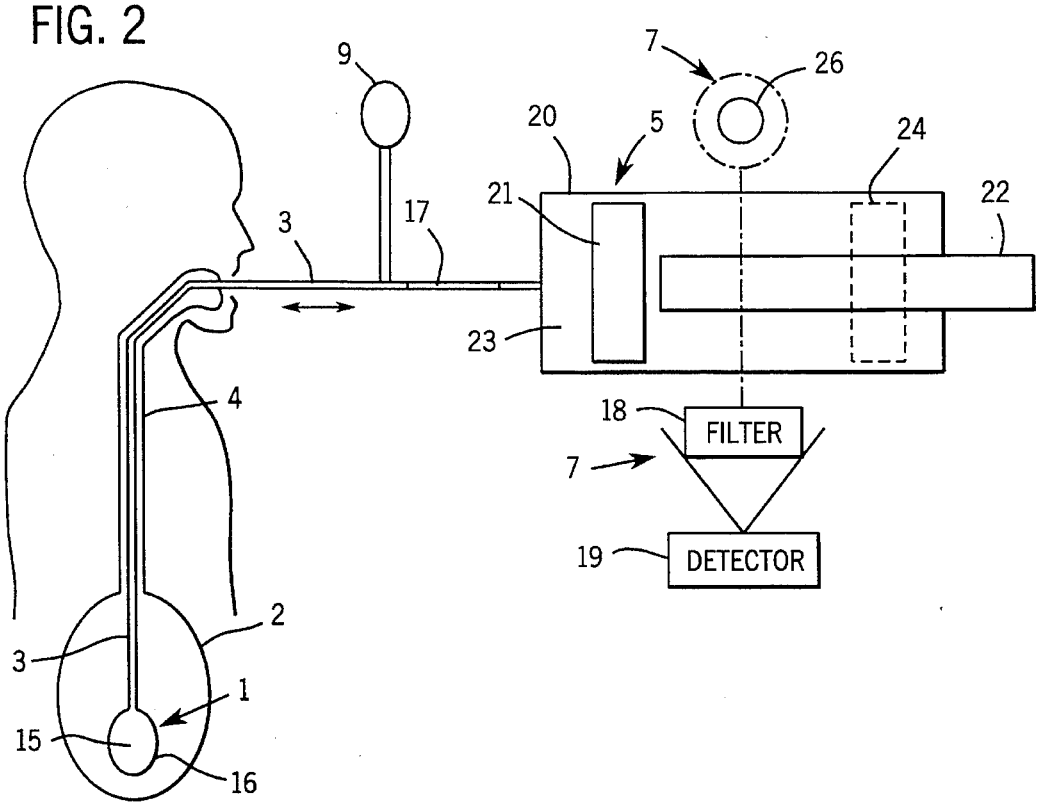

FIG. 2 illustrates another highly useful solution for analyzing a sample drawn from the organ of a patient. In this embodiment, a sample mixed in a medium is delivered from a sampling element 1 to a pressure-difference producing element 5 and back along a common tube 3. A pressure-detecting element 9, as well as preferably also a tube 17 of a water-vapor permeable material, are fitted between the pressure-difference producing element and the sampling element.

A pressure-difference producing element 5, which can be manually or electrically operated, and an analyzer 7 are combined in FIG. 2. The analyzer comprises a radiation source 26 for emitting preferably infrared radiation when analyzing carbon dioxide, a filter 18, and a radiation receiver 19 or a detector. On the other hand, the pressure-difference producing element 5 comprises a housing portion 20, carrying therein a piston 21 which travels back and forth under the control of an element 22, coupled to the piston and controlling its movement. As the piston is operated so as to increase a volume extending from sampling element 1 to piston 21, the piston moving rearwards in the solution shown in FIG. 2, a sample will be aspirated from the sampling element into a chamber 23 defined by housing portion 20 and piston 21. In FIG. 2, the piston position at the time when a sufficient amount of sample has been received in chamber 23, increasing in size as a result of the piston action, is indicated by dotted lines 24. On the other hand, in relation to pressure-difference producing element 5, the analyzer is positioned in a manner that the radiation source 26 and the radiation detector are located on the opposite sides of housing portion 20, whereby a beam traveling from the radiation source to the radiation receiver runs through chamber 23 as well as housing portion 20. At least within the zone of contact with the traveling beam, the housing portion consists of a material which is transmissible to the radiation directed from the radiation source to detector. Hence, at this point, a sample containing a compound to be examined is subjected to a content measurement and preferably also to a pressure measurement with pressure-measuring element 9 for detecting a pressure prevailing in chamber 23 in view of carrying out a pressure compensation for the content measurement result. When piston 21 is in its forward-pushed position, i.e. a sample is forced back into the sampling element, there is effected a zero-gas control, since the volume of chamber 23 has been reduced so as not to extend any longer to a location between radiation source 26 and detector 19.

Figure 3:
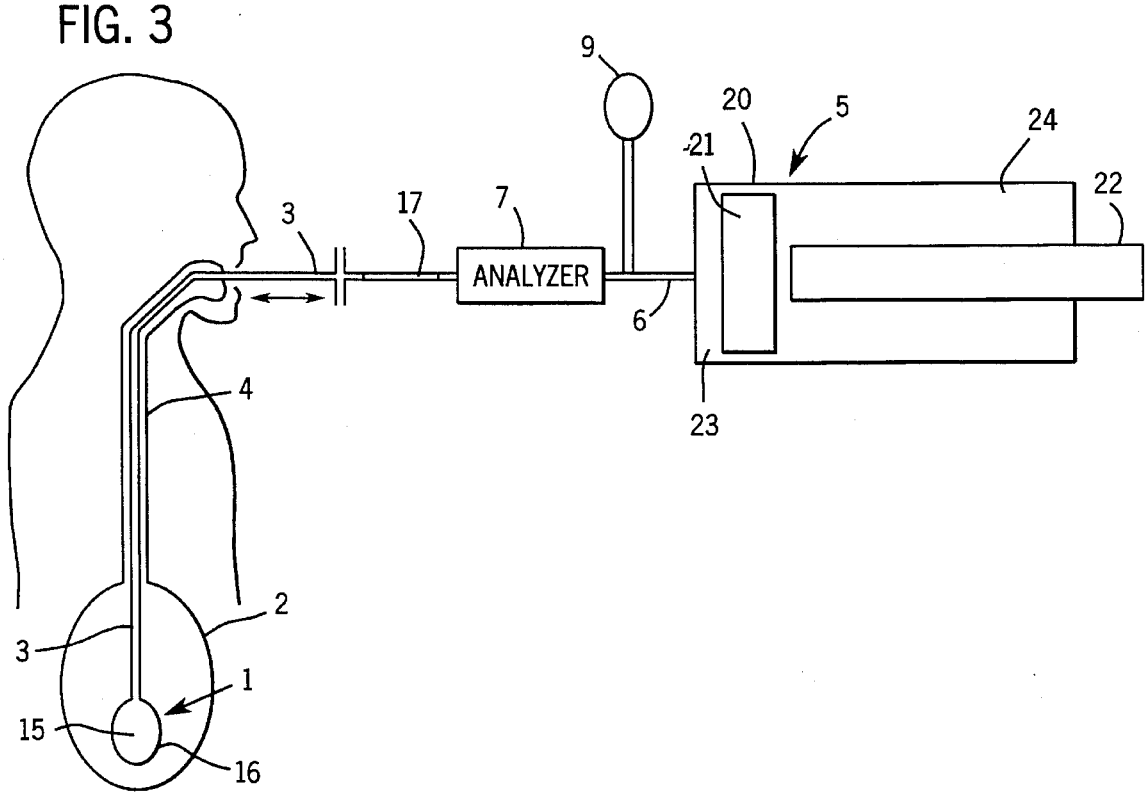

FIG. 3 shows an alternative embodiment of the invention utilizing the pressure-difference producing element 5 of the type shown in FIG. 2, but in which separate analyzer 7 is placed upstream of the pressure-difference producing element 5, in the flow direction of the sample from the sampling element to the pressure-difference producing element.

FIG. 3 illustrates a solution resembling that of FIG. 2, the main difference being that analyzer 7 and pressure-difference producing element 5 are spaced from each other and pressure-measuring element 9 is coupled there between in tube 6. Also in this case, the flow of a sample between sampling element 1 and analyzer proceeds in both directions along a common tube 3. Preferably, said tube 3 is fitted with a tube 17, made of a water-vapor permeable material and reducing the amount of water vapor carried along with a sample and finding its way to the analyzer. A sample contained in the sampling element is aspirated by means of a piston 21 included in pressure-difference producing element 5 to analyzer 7 for the measurement of carbon dioxide content. At this point, said pressure-measuring element 9 performs a pressure measurement, so that a pressure reading affecting the analyzing result could be corrected from this result. After the measurement is completed, the gas sample is forced by means of piston 21 back to the sampling element to stand by for another measurement. Thus, the construction and operation of a pressure-difference producing element are otherwise similar to those described in connection with FIG. 2 except that there is no need for the solutions made for an analyzer connected to this element in FIG. 2.

The invention is by no means limited to the above embodiments but various details of the invention can be modified within the scope of the annexed claims. It is also possible to deliver a fresh batch of medium to the sampling element after aspirating the mixture of a medium and a compound to be examined therefrom to the analyzer, if that should be necessary for some reason.

I claim:

1. Apparatus for analyzing a fluid substance found in a patient's organ (2), said apparatus comprising:

a sampling element (1) having a generally enclosed sampling chamber (15) with a wall (16) across which the substance to be analyzed may pass between the organ and said sampling chamber;

a pressure-difference producing element (5) coupled to said sampling chamber by a conduit means (3), said pressure-difference producing element creating a pressure difference for withdrawing a sample of the contents of said sampling chamber from said sampling chamber along said conduit means;

an analyzer (7) coupled to said pressure-difference producing element for receiving the sample withdrawn from said sampling chamber to obtain a sample analysis result; and pressure measuring means coupled to said analyzer for measuring the pressure on the sample and for providing a pressure measurement result, said analyzer altering the analysis result in accordance with the pressure measurement result.

2. The apparatus according to claim 1 wherein said pressure measuring means is further defined as measuring the pressure on the sample during the analysis thereof.

3. The apparatus according to claim 1 wherein said analyzer is further defined as altering the analysis result in accordance with the difference between the measured pressure and a predetermined pressure condition.

4. The apparatus according to claim 1 wherein said sampling chamber is further defined as containing a fluid medium for admixing with said fluid substance.

5. The apparatus according to claim 1 wherein said conduit means is further defined as means for returning at least a portion of the withdrawn sample to said sampling chamber from said analyzer.

6. The apparatus according to claim 5 wherein said conduit means is further defined as including a pair of generally adjacent conduits, the withdrawn sample passing along one of said conduits, the at least a portion of the withdrawn sample returned to said sampling chamber passing along the other of said conduits.

7. The apparatus according to claim 1 wherein said analyzer is further defined as interposed in said conduit means between said sampling chamber and said pressure-difference producing element.

8. The apparatus according to claim 1 wherein said pressure-difference producing element comprises a housing coupled to said conduit means, said housing having a piston reciprocally movable therein for creating said pressure difference.

9. The apparatus according to claim 8 wherein said analyzer is further defined as interposed in said conduit means between said sampling chamber and said pressure-difference producing element.

10. The apparatus according to claim 5 wherein said pressure difference producing element comprises a housing coupled to said conduit means, said housing having a piston reciprocally movable therein for creating a pressure-difference for withdrawing the sample from said sampling chamber and a pressure-difference for returning at least a portion of the withdrawn sample to said sampling chamber.

11. The apparatus according to claim 1 wherein said analyzer is coupled to said pressure-difference producing element, said pressure-difference producing element having means providing a radiation path through said sample between a radiation source and a radiation detector of said analyzer.

12. The apparatus according to claim 1 further including water permeable means coupled to said sampling chamber at a location exposed to ambient air for balancing the water vapor concentration of the sample with the water vapor concentration of the ambient air.

13. The apparatus according to claim 12 wherein said water permeable means is located in said conduit means.

14. The apparatus of claim 1 wherein said sampling chamber is further defined as suitable for insertion in the stomach of the patient.

15. The apparatus according to claim 1 further defined as one for measuring the quantity of the substance in the sample.

16. The apparatus according to claim 15 wherein the sample contains a substance comprising $CO_2$ and the apparatus is further defined as one for measuring the quantity of $CO_2$ in the sample.

17. Apparatus for analyzing a fluid substance found in a patient's organ (2), said apparatus comprising:
a sampling element (1) having a generally enclosed sampling chamber (15) with a wall (16) across which the substance to be analyzed may pass between the organ and said sampling chamber:

a pressure-difference producing element (5) coupled to said sampling chamber by a conduit means (3), said pressure-difference producing element creating a pressure difference for withdrawing a sample of the contents of said sampling chamber from said sampling chamber along said conduit means;

an analyzer (7) coupled to said pressure-difference producing element for receiving the sample withdrawn from said sampling chamber to obtain a sample analysis result; and water permeable means coupled to said sampling chamber at a location exposed to ambient air for balancing the water vapor concentration of the sample with the water vapor concentration of the ambient air.

18. The apparatus according to claim 17 wherein said water permeable means is located in said conduit means.

19. A method for analyzing a fluid substance found in a patient's organ, said method comprising the steps of:
forming a sampling chamber in the patient's organ that is permeable to the substance;

providing a fluid medium in the sampling chamber;

allowing the substance to pass between the organ and the sampling chamber for admixing with the fluid medium;

withdrawing a sample of the contents of the sampling chamber and passing the sample along a conduit means to an analyzer;

measuring the pressure existing on the sample to produce a measurement result;

analyzing the withdrawn sample to produce an analysis result; and altering the analysis result in accordance with the pressure measurement result.

20. The method according to claim 19 further defined as altering the analysis result in accordance with the difference between the measured pressure and a predetermined pressure condition.

21. The method according to claim 19 further defined as measuring the pressure on the sample during the analysis thereof.

22. The method according to claim 19 further defined as creating a pressure difference in the sample chamber for withdrawing the sample.

23. The method according to claim 19 further defined as including the step of returning at least a portion of the withdrawn sample to the sampling chamber.

24. The method according to claim 23 wherein the withdrawal of the sample and the return of at least a portion of the withdrawn sample occur in a single conduit connected to the sampling chamber.

25. The method according to claim 23 wherein the withdrawal of the sample occurs in one conduit connected to said sampling chamber and the return of at least a portion of the withdrawn sample occurs in another conduit connected to the sample chamber.

26. The method according to claim 23 further defined as allowing the concentration of the substance in the contents of the sampling chamber to change toward the concentration existing in the organ.

27. The method according to claim 23 further defined as withdrawing a further sample from the sampling chamber following the return of at least a portion of the withdrawn sample to the sample chamber.

28. The method according to claim 19 further including the step of balancing the water vapor concentration of the sample with the water vapor concentration of ambient air prior to providing the sample to the analyzer.

29. The method according to claim 28 wherein the step of balancing the water vapor concentration of the sample with the water vapor concentration of ambient air is further defined as passing the sample past one surface of a member permeable to water vapor, another surface of said member being exposed to ambient air.

30. The method according to claim 19 further defined as intermittently providing samples to the analyzer.

31. The method according to claim 19 further defined as continuously providing a sample to the analyzer.

32. The method according to claim 31 further defined as withdrawing a further sample from the sampling chamber following the return of at least a portion of the withdrawn sample to the sampling chamber.

33. The method according to claim 19 further defined as forming a sampling chamber in the patient's stomach.

34. The method according to claim 19 further defined as one for measuring the quantity of the substance in the sample.

35. The method according to claim 34 wherein the sample contains a substance comprising $CO_2$ and wherein the method is further defined as one for measuring the quantity of $CO_2$ in the sample.

36. A method for analyzing a fluid substance found in a patient's organ, said method comprising the steps of:

forming a sampling chamber in the patient's organ that is permeable to the substance;

providing a fluid medium in the sampling chamber;

allowing the substance to pass between the organ and the sampling chamber for admixing with the fluid medium;

withdrawing a sample of the contents of the sampling chamber;

balancing the water vapor concentration of the sample with the water vapor concentration of ambient air; and passing the sample along a conduit means to an analyzer.

37. The method according to claim 36 wherein the step of balancing the water vapor concentration of the sample with the water vapor concentration of ambient air is further defined as passing the sample past one surface of a member permeable to water vapor, another surface of said member being exposed to ambient air.

* * * * *